United States Patent [19]

Moeller et al.

[11] Patent Number: 4,613,622
[45] Date of Patent: Sep. 23, 1986

[54] SEBOSUPPRESSIVE PREPARATIONS CONTAINING BENZYL ALCOHOL DERIVATIVES

[75] Inventors: Hinrich Moeller; Siegfried Wallat, both of Monheim, Fed. Rep. of Germany

[73] Assignee: Henkel Kommanditgesellschaft auf Aktien, Duesseldorf, Fed. Rep. of Germany

[21] Appl. No.: 646,173

[22] Filed: Aug. 30, 1984

[30] Foreign Application Priority Data

Sep. 9, 1983 [DE] Fed. Rep. of Germany ....... 3332507

[51] Int. Cl.$^4$ .................. A61K 31/075; A61K 31/045
[52] U.S. Cl. .................................... 514/718; 514/730; 514/864; 514/852
[58] Field of Search ................ 424/339, 343; 514/730, 514/864, 852, 718

[56] References Cited

U.S. PATENT DOCUMENTS

| | | | |
|---|---|---|---|
| 3,663,716 | 5/1972 | Stolar | 424/343 |
| 3,949,072 | 4/1976 | Tenta | 424/343 |
| 4,219,570 | 8/1980 | Inazuka et al. | 424/343 |
| 4,331,655 | 5/1982 | Tur | 424/59 |
| 4,562,068 | 12/1985 | Moeller et al. | 424/70 |

OTHER PUBLICATIONS

Mutation Research, 100 (1982), 1–6 Ashby et al.
Ashby et al., Chem. Abst. 96:117284u (1982).
Coombs, Chem. Abst. 96:117285v (1982).
Coombs, Chem. Abst. 96:117286w (1982).
Otsuka, Chem. Abst. 99:38363(c) (1982).

*Primary Examiner*—Albert T. Meyers
*Assistant Examiner*—F. Abramson
*Attorney, Agent, or Firm*—Ernest G. Szoke; Henry E. Millson, Jr.; Mark A. Greenfield

[57] ABSTRACT

Sebosuppressive cosmetic preparations containing benzyl alcohol derivatives which are substituted on the benzene ring by alkyl, aryl, alkyloxymethyl radicals or by a fused aromatic ring, and methods for their use.

30 Claims, No Drawings

SEBOSUPPRESSIVE PREPARATIONS CONTAINING BENZYL ALCOHOL DERIVATIVES

BACKGROUND OF THE INVENTION

1. Field of the Invention

This invention relates to certain benzyl alcohol derivatives and their use in topical preparations for improving an oily and unaesthetic appearance of the hair and skin.

2. Statement of the Related Art

In modern cosmetology, efforts are constantly being made to reduce the oily, unaesthetic appearance of the hair and scalp caused by excessive secretion of the sebaceous glands. Accordingly, frequent attempts have been made to normalize (i.e. reduce) the secretion of the sebaceous glands by suitable preparations in order to restore the skin and hair to its healthy appearance. Cosmetic preparations containing additions of sulfur, mercury or tar have been used to control seborrhea of the scalp. Unfortunately, it has been found that these known antiseborrheic additives frequently produce side effects after prolonged use, without giving really satisfactory results in regard to efficacy and performance properties. U.S. Pat. No. 4,331,655 and corresponding German Patent Application 29 26 267 describe 3,7,11-tri:methyl-2,6,10-dodecatri:en-1-ol ethyl ether and/or acetate as additives to cosmetic preparations for normalizing the secretion of sebum. Unfortunately, it has been found that these compounds have only a very weak antiseborrheic effect.

It is therefore highly desirable to provide a cosmetic preparation which has a stronger effect than corresponding known preparations without any adverse consequences on the human body.

DESCRIPTION OF THE INVENTION

It has now surprisingly been found that certain benzyl alcohol derivatives show outstanding antiseborrheic effects, even in very small doses.

Accordingly, the present invention relates to sebocosmetic preparations which are characterized by an effective sebosuppressive content of at least one benzyl alcohol derivative corresponding to the following general formula

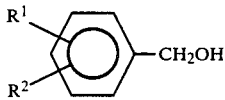

in which $R^1$ is a linear or branched $C_{4-18}$ alkyl, an aryl (preferably phenyl), or a $C_{4-18}$-alkyl-oxymethyl radical, $R^2$ is H, or $R^1$ and $R^2$ together form a fused aromatic ring (preferably a benzene ring), $R^1$ occupying the 2-, 3- or 4- (preferably the 4-) position.

Most of the benzyl alcohol derivatives used in accordance with the invention are known and may be produced by generally known methods.

One method of production is based on hydrolysis of the corresponding benzyl halides, advantageously proceeding by way of the benzyl acetate intermediate. The benzyl halides may be obtained from the correspondingly substituted aromatic compounds by halomethylation, preferably chloromethylation.

Another method of production is based on the reduction of suitable aromatic carboxylic acid esters or aldehydes. Reduction may be carried out not only by catalytic hydrogenation, but also using complex metal hydrides, such as sodium borohydride, lithium aluminium hydride and sodium-bis-(2-methoxyethoxy)-aluminium dihydride.

The following are exemplary of benzyl alcohol derivatives which may be used in accordance with the invention, and are not intended to be limiting:

4-butyl-, 4-sec.-butyl-, 4-tert.-butyl-, 4-phenyl-, 4-hexyl-, 4-pentyl-, 4-octyl, 2-octyl-, 4-decyl-, 3-decyl, 4-dodecyl-, 4-undecyl-, 4-tetradecyl, 4-hexadecyl-, 4-octadecyl-, 4-(2-ethylhexyl)-, 4-isononyl-, 4-(2-hexyldecyl)-, 4-decyloxymethyl-, 4-dodecyloxymethyl-benzyl alcohol and also 1- and 2-hydroxymethyl naphthalene.

The compounds according to the invention show pronounced sebosuppressive activity combined with excellent compatibility with the skin and mucous membrane. They may be incorporated without difficulty in various cosmetic preparations, such as aqueous or alcoholic solutions, oils, suspensions, gels, emulsions, salves or aerosols. For treating seborrheic skin and oily hair, these preparations may be applied in any of the usual forms, such as hair lotions, shampoos, hair treatments, hair rinses, skin lotions or shaking mixtures. They are preferably used in hair care preparations. In addition to the active substance combination according to the invention, these cosmetic preparations may contain standard auxiliaries and vehicles, such as water, organic solvents, surfactants, oils, fats, waxes, frangrances, dyes, preservatives and the like. The new sebosuppressive compositions contain about from 0.01 to 5.0% by weight and preferably about from 0.05 to 1% by weight of the benzyl alcohol derivatives. Unless otherwise indicated, all percentages are by weight based upon the total weight of the composition.

PRODUCTION EXAMPLES FOR BENZYL ALCOHOL DERIVATIVES

(A) 4-octylbenzyl alcohol

A mixture of 16.2 g (68 mMols) of 4-octylbenzyl chloride, 41,8 g (0.43 mols) of potassium acetate and 200 ml of glacial acetic acid was heated for 20 h to 130° C. After cooling, the mixture was poured into approximately 1 liter of water and the aqueous phase was extracted with tert.-butyl methyl ether. The organic phase was washed twice with water, repeatedly with potassium hydrogen carbonate solution (2N) and then with saturated sodium chloride solution. After the solvent had been distilled off, the residue was taken up in 160 ml of 1,2-dimethoxyethane and, after the addition of 64 g of sodium hydroxide in 130 ml of water, the solution was heated for 45 h to boiling point. After the solvent had been distilled off, the residue was extracted with tert.-butyl methyl ether, the ether phase was washed with water, the solvent was distilled off, the residue was taken up in petroleum ether and the solution was reconcentrated by evaporation after treatment with active carbon and fuller's earth. Fractionation under reduced pressure produced 8 g (54% of theoretical) of 4-octylbenzyl alcohol boiling at 128° C./0.11 mbar and having a refractive index n of 1.5033.

(B) 4-decylbenzyl alcohol was obtained in the same way as (A): M.p. 39°–40° C.

(C) 4-dodecylbenzyl alcohol was obtained in the same way as (A): M.p. 44°–45° C.

(D) 4-decyloxymethylbenzyl alcohol 0.25 g (6.7 mMols) of sodium borohydride and 0.58 g (6.7 mMols) of lithium bromide were added to 20 ml of diethylene glycol dimethyl ether. After stirring for 30 minutes, 3.3 g (10.8 mMols) of 4-decyloxymethyl benzoic acid methyl ester (from 4-hydroxymethylbenzoic acid methyl ester and decyl bromide were added. The mixture was heated for 3.5 h with stirring to 100° C., cooled and poured in portions onto ice.

After the aqueous phase had been acidified with 1.5 ml of concentrated hydrochloric acid, the reaction product was extracted with methylene chloride and, after concentration of the methylene chloride solution by evaporation, was subjected to column chromatography (SiO/methylene chloride+1% of methanol). After unreacted starting material had first been eluted, 1 g of 4-decyloxymethylbenzyl alcohol melting at 20° to 31° C. was obtained from the subsequent fractions.

(E) 4-phenylbenzyl alcohol and (F) 4-tert.-butylbenzyl alcohol are commercially available.

Use of the Compositions

The antiseborrheic effect was closely studied using the animal tests described in the following:

The test animals were male Wistar rats having a body weight of 220 to 230 g. The degree of browning on the shaved back of the rats was visually assessed. Browning is produced by the brown skin surface lipids of the rats. This test is based on the observation that young male and female rats washed with surfactant solution or with a lipid solvent and also male rats systematically treated with oestrogen have only the normal light, pick-colored skin after shaving. At the same time, only comparatively very small quantities of lipids can be extracted from shaved hairs.

In order to assess effectiveness, the test substances in solution in alcohol were each brushed onto half the back of 6 rats. The other half was only treated with the solvent minus active substances.

Over the test period of 14 days, the test substances were applied once daily for a total of 9 days. A group of 6 rats which remained completely untreated was used for further control. At the end of the test, the animals were shaved on their back and sides and were visually assessed independently by an examination panel of 6 people under double blind conditions.

Evaluation methods

The first criterion evaluated was whether the majority of examiners correctly recognized the treated side, differentiation being carried out as follows:

| Symbol | Percentage of examiners, noticing an effect |
| --- | --- |
| ++ | 100% |
| + | >50%–100% |
| 0 | ≧50% |

The second criterion evaluated was the difference between the righthand side and the lefthand side, each examiner having to award 1 point per animal on the following basis:

| | |
| --- | --- |
| darker side | 1 point |
| lighter side | 0 point and |
| both sides the same | 0.5 point |

Significant differences between the untreated and treated sides in the second method of evaluation indicated the local effectiveness of a substance.

The third criterion evaluated was the difference in intensity between the shades of brown using the following scale:

| | |
| --- | --- |
| 3 points | dark brown |
| 2 points | medium brown |
| 1 point | light brown |
| 0 points | no browning |

In the third method of evaluation, the total point differences are compared between the untreated control animals and the treated and untreated sides of the test animals, significant differences between the control animals and the treated side of the test animals again indicating the effectiveness of a substance.

There is generally also a distinct difference between the untreated and treated sides of the same test animals. However, this difference is not always as clear as that between the control animals and the treated sides, for which there may be various reasons, such as mechanical transfer of substance from one side to the other or solvent influence.

The following scheme was used for differentiating the effects according to evaluation methods 2 and 3:

| Symbol | Points difference |
| --- | --- |
| ++ | very large (≧99.9% probability) |
| + | significant (≧95% probability) |
| 0 | minimal (<95% probability) |

Percentage sebum reduction

The sebum reduction is calculated from the points difference by working out the quotient between the points difference ΔP and the number of points for the control group $P_k$, and expressing the value obtained in percent.

$$\text{Sebum reduction} = \frac{\Delta P}{P_k} \cdot 100[\%]$$

The benzyl alcohol derivatives were applied in the manner described in concentrations of 0.5 and 1.0% in alcohol/acetone (1:1). The results are given in the following Table.

TABLE

| | | Evaluation of sebosuppressive effects | | | |
| --- | --- | --- | --- | --- | --- |
| | Conc. | Evaluation method | | | Sebum reduction |
| Compound | (%) | 1 | 2 | 3 | (%) |
| A | 0.5 | ++ | ++ | ++ | 94 |
| B | 0.5 | ++ | ++ | ++ | 95 |
| C | 0.5 | ++ | ++ | ++ | 32 |
| D | 0.5 | ++ | ++ | ++ | 82 |
| E | 0.5 | ++ | ++ | ++ | 72 |

TABLE-continued

| | Evaluation of sebosuppressive effects | | | | |
|---|---|---|---|---|---|
| | Conc. | Evaluation method | | | Sebum reduction |
| Compound | (%) | 1 | 2 | 3 | (%) |
| F | 1.0 | ++ | ++ | ++ | 56 |
| Benzyl alcohol (according to U.S. Pat. No. 3,663,716) | 1.0 | 0 | 0 | 0 | 0 |

In the above Table, preferred sebum reduction is at least 50%, more preferred is at least 80% and most preferred is at least 90%.

Examples of cosmetic formulations

Formulations for topical preparations according to the invention for the treatment of very oily hair and seborrheic skin are given in the following:

| | Parts by weight |
|---|---|
| 1. Shampoo for oily hair | |
| Ammonium lauryl sulfate containing 33–35% of wash-active substance (Texapon A) | 40.0 |
| Coconut oil fatty acid diethanolamide (Comperlan KD) | 3.0 |
| Sodium chloride | 2.0 |
| Sodium sulfate | 2.0 |
| 4-decylbenzyl alcohol (INVENTION COMPOUND B) | 0.5 |
| Preservative | 0.1 |
| Perfume oil | 0.1 |
| Water | 52.3 |
| 2. Hair Treating Agent | |
| Glycerol mono-distearate (Tegin M) | 0.7 |
| Cetyltrimethylammonium chloride cationic surfactant (Dehyquart A) | 2.0 |
| Chlolesterol | 2.0 |
| Soya lethicin | 0.2 |
| a mixture of cetyl alcohol with nonionic emulsifiers (Emulgade A) | 8.0 |
| Perfume oil | 0.3 |
| 4-decyloxymethylbenzyl alcohol (INVENTION COMPOUND D) | 0.2 |
| Water, fully deionized | 88.3 |
| 3. Skin cream | |
| Self-emulsifying mixture of mono/di-glycerides of higher saturated fatty acids with potassium stearate (Cutina KD 16) | 16.0 |
| Cetyl stearyl alcohol containing approximately 10 12 moles of ethylene oxide (Eumulgin B 1) | 1.0 |
| 2-octyldodecanol | 8.0 |
| Isopropyl myristate | 6.0 |
| Glycerol | 6.0 |
| 4-octylbenzyl alcohol (INVENTION COMPOUND A) | 0.2 |
| Water | 62.8 |

Suppliers of the trademarked products mentioned:
Texapon A = Henkel KGaA, Germany
Comperlan KD = Henkel KGaA
Cutina KD 16 = Henkel KGaA
Emulgade A = Henkel KGaA
Eumulgin B 1 = Henkel KGaA
Tegin M = Atlas Chemie, Germany
Dehyquart A = Henkel KGaA The foregoing formulations are conventional except for the inclusion of the inventive sebosuppressive compound. The nature and amounts of the sebosuppressive compound need not vary, regardless of whether the formulations are for shampoos, hair treating agents, or skin creams. All formulations, regardless of use, are preferably water-based. Shampoos, cleansing creams, etc., should contain at least one surfactant.

Skin creams should contain emollients such as mono- or di-glycerides of saturated higher fatty acids, preferably with a suitable emulsifier.

It is also possible for the sebosuppressive compounds of this invention to be used in a pharmaceutical manner, when applied in a pharmaceutically effective sebosuppressive amount, and in a suitable carrier or adjuvant.

The method of treating seborrheic skin, scalp or hair conditions using the inventive compositions is to apply each formulation in the same manner it would be applied if it were not sebosuppressive.

We claim:

1. A method of treating seborrheic skin or hair comprising the topical application to an individual in need of such treatment of a composition containing a sebosuppressive effective amount of at least one compound of the formula

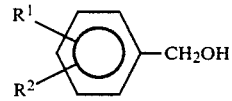

wherein:
$R^1$ is a linear or branched $C_{4-18}$-alkyl, phenyl, or a $C_{4-18}$-alkyl-oxy-methyl radical, and occupies the 2,3 or 4 positions; and
$R^2$ is H or forms a fused aromatic ring with $R^1$.

2. The method of claim 1 wherein $R^1$ occupies the 4 position.

3. The method of claim 1 wherein $R^1$ and $R^2$ form a benzene ring.

4. The method of claim 1 where $R^1$ is phenyl.

5. The method of claim 1 wherein said compound is at least one of 4-butyl-, 4-phenyl-, 4-hexyl-, 4-pentyl-, 4-octyl-, 2-octyl-, 4-decyl-, 3-decyl-, 4-dodecyl-, 4-undecyl-, 4-tetradecyl-, 4-hexadecyl-, 4-octadecyl-, 4-(2-ethoxyhexyl)-, 4-isononyl-, 4-(2-hexyldecyl)-, 4-decyloxymethyl-, or 4-dodecyloxymethyl-benzyl alcohol; or 1- or 2-hydroxymethylnaphthalene.

6. The method of claim 1 wherein said compound is at least one of: 4-octylbenzyl alcohol; 4-decylbenzyl alcohol; 4-dodecylbenzyl alcohol; 4-decyloxymethylbenzyl alcohol; 4-phenylbenzyl alcohol, or 4-tert.-butyl benzyl alcohol.

7. The method of claim 1 wherein said compound is present in about 0.01 to 5.0% by weight, based upon the total weight of the composition.

8. The method of claim 1 wherein said compound is present in about 0.05 to 1% by weight, based upon the total weight of the composition.

9. The method of claim 1 wherein said composition is a sebosuppressive shampoo for oily hair and treatment is by the shampooing of the said hair with said composition.

10. The method of claim 1 wherein said composition is a sebosuppressive hair treating composition and treatment is by the application of said composition to said hair.

11. The method of claim 1 wherein said composition is a sebosuppressive skin cream and treatment is by application of said cream to the skin.

12. The method of claim 2 wherein said composition is a sebosuppressive shampoo for oily hair and treatment is by the shampooing of the said hair with said composition.

13. The method of claim 2 wherein said composition is a sebosuppressive hair treating composition and treatment is by the application of said composition to said hair.

14. The method of claim 2 wherein said composition is a sebosuppressive skin cream and treatment is by application of said cream to the skin.

15. The method of claim 3 wherein said composition is a sebosuppressive shampoo for oily hair and treatment is by the shampooing of the said hair with said composition.

16. The method of claim 3 wherein said composition is a sebsuppressive hair treating composition and treatment is by the application of said composition to said hair.

17. The method of claim 3 wherein said composition is a sebosuppressive skin cream and treatment is by application of said cream to the skin.

18. The method of claim 4 wherein said composition is a sebosuppressive shampoo for oily hair and treatment is by the shampooing of the said hair with said composition.

19. The method of claim 4 wherein said composition is a sebosuppressive hair treating composition and treatment is by the application of said composition to said hair.

20. The method of claim 4 wherein said composition is a sebosuppressive skin cream and treatment is by application of said cream to the skin.

21. The method of claim 5 wherein said composition is a sebosuppressive shampoo for oily hair and treatment is by the shampooing of the said hair with said composition.

22. The method of claim 5 wherein said composition is a sebosuppressive hair treating composition and treatment is by the application of said composition to said hair.

23. The method of claim 5 wherein said composition is a sebosuppressive skin cream and treatment is by application of said cream to the skin.

24. The method of claim 6 wherein said composition is a sebosuppressive shampoo for oily hair and treatment is by the shampooing of the said hair with said composition.

25. The method of claim 6 wherein said composition is a sebosuppressive hair treating composition and treatment is by the application of said composition to said hair.

26. The method of claim 6 wherein said composition is a sebosuppressive skin cream and treatment is by application of said cream to the skin.

27. The method of claim 7 wherein said composition is a sebosuppressive shampoo for oily hair and treatment is by the shampooing of the said hair with said composition.

28. The method of claim 7 wherein said composition is a sebosuppressive hair treating composition and treatment is by the application of said composition to said hair.

29. The method of claim 7 wherein said composition is a sebosuppressive skin cream and treatment is by application of said cream to the skin.

30. The method of claim 1 wherein said compound is at least one of: 4-octylbenzyl alcohol, 4-decylbenzyl alcohol, or 4-decyloxymethylbenzyl alcohol.

* * * * *